United States Patent
Hall et al.

(10) Patent No.: US 10,145,856 B2
(45) Date of Patent: Dec. 4, 2018

(54) DRUG TRACKING SYSTEM INCLUDING FOOD DYES DETECTABLE IN BODILY WASTE

(71) Applicants: David R. Hall, Provo, UT (US); Steven J. M. Butala, Provo, UT (US); Daniel R. Hendricks, Provo, UT (US); Andrew Huy Nguyen, Spanish Fork, UT (US); A. Terrece Pearman, Riverton, UT (US)

(72) Inventors: David R. Hall, Provo, UT (US); Steven J. M. Butala, Provo, UT (US); Daniel R. Hendricks, Provo, UT (US); Andrew Huy Nguyen, Spanish Fork, UT (US); A. Terrece Pearman, Riverton, UT (US)

(73) Assignee: Hall Labs, LLC, Provo, UT (US)

( * ) Notice: Subject to any disclaimer, the term of this patent is extended or adjusted under 35 U.S.C. 154(b) by 0 days.

(21) Appl. No.: 15/892,834

(22) Filed: Feb. 9, 2018

(65) Prior Publication Data

US 2018/0275152 A1    Sep. 27, 2018

Related U.S. Application Data

(63) Continuation-in-part of application No. 15/465,939, filed on Mar. 22, 2017, now Pat. No. 9,927,448.

(51) Int. Cl.
| | | |
|---|---|---|
| *G01N 33/94* | (2006.01) | |
| *G01N 33/483* | (2006.01) | |
| *G01N 33/493* | (2006.01) | |
| *G01N 33/58* | (2006.01) | |
| *G01N 21/25* | (2006.01) | |
| *G01N 21/31* | (2006.01) | |
| *G01N 21/80* | (2006.01) | |

(52) U.S. Cl.
CPC ............. *G01N 33/94* (2013.01); *G01N 21/25* (2013.01); *G01N 21/31* (2013.01); *G01N 33/4833* (2013.01); *G01N 33/493* (2013.01); *G01N 33/583* (2013.01); *G01N 21/80* (2013.01); *G01N 2021/3196* (2013.01); *Y10T 436/13* (2015.01)

(58) Field of Classification Search
CPC ...... G01N 33/48; G01N 33/493; G01N 33/94; G01N 21/31; G01N 21/3103; G01N 21/33; G01N 21/35; G01N 21/25; G01N 33/4833; G01N 33/583; G01N 21/80; G01N 2021/3196; Y10T 436/13
USPC .................. 436/56, 63, 163, 164, 171, 901; 422/82.05, 82.09; 435/29
See application file for complete search history.

(56) References Cited

U.S. PATENT DOCUMENTS

| | | | | |
|---|---|---|---|---|
| 3,341,417 A | * | 9/1967 | Sinaiko | A61K 49/0404 116/201 |
| 6,383,736 B1 | * | 5/2002 | Titmas | G01N 33/523 435/283.1 |
| 9,671,343 B1 | * | 6/2017 | Hall | G01N 21/6428 |
| 9,766,257 B1 | * | 9/2017 | Hall | G01N 33/94 |
| 9,927,448 B1 | * | 3/2018 | Hall | G01N 33/94 |
| 9,970,949 B1 | * | 5/2018 | Hall | G01N 33/15 |
| 2002/0173042 A1 | * | 11/2002 | Oolman | G01N 33/02 436/56 |
| 2004/0228802 A1 | * | 11/2004 | Chang | A61K 9/2013 424/10.2 |
| 2006/0039865 A1 | * | 2/2006 | Preston | A61K 31/46 424/10.4 |
| 2015/0202588 A1 | * | 7/2015 | Allphin | A61K 31/19 514/282 |
| 2015/0369794 A1 | * | 12/2015 | Keller | G01N 33/9486 435/14 |
| 2016/0109371 A1 | * | 4/2016 | Blair | G01N 21/645 436/172 |

FOREIGN PATENT DOCUMENTS

GB    2309166    *    7/1997

* cited by examiner

*Primary Examiner* — Maureen Wallenhorst

(57) ABSTRACT

The drug tracking system may be used to screen a subject's bodily waste and to identify a drug the subject has consumed. The system includes drug tags which include a one or more food dyes, each detectable in a subject's bodily waste using photographic or absorption spectroscopic analysis. The system may further include a database in which is stored the spectral signature of each drug tag and the unique drug associated with each drug tag. A spectral analysis obtained by analyzing a bodily waste sample may be entered into the database. The database may include instructions for comparing the spectral analysis to the spectral signature of each drug tag. The instructions may further report the unique drug associated with a drug tag which has a spectral signature matching the spectral analysis.

18 Claims, 8 Drawing Sheets

DRUG TRACKING SYSTEM INCLUDING FOOD DYES DETECTABLE IN BODILY WASTE

CROSS REFERENCE TO RELATED APPLICATIONS

This application is a continuation in part of U.S. patent application Ser. No. 15/465,939 filed on Mar. 22, 2017, now U.S. Pat. No. 9,927,448, which is hereby incorporated by reference in its entirety.

BACKGROUND

Field of the Invention

This disclosure relates to methods of tracking and identifying pharmaceuticals after consumption, particularly by screening bodily waste for drug tags.

Background of the Invention

The consumption of drugs is largely untracked. This is problematic for dealing with issues such as opiate addiction, sharing of prescriptions, counterfeit drugs, consumption of contraindicated drugs, consumption of multiple drugs with adverse interactions, drug allergies, dosing control and adjustment, emergency medicine and many other situations. It is also difficult to interpret clinical studies when drug compliance of study subjects is inconsistent.

Tracking of drugs in the human waste stream is desirable. Drug tracking molecules that do not have negative physiological effects and have little to no drug interactive effects are also desirable. A drug tracking molecule that is commonly found in food would be an attractive candidate, particularly when it is possible to detect the drug tracking molecule in the human waste stream using noninvasive and well-established analytical methods.

BRIEF SUMMARY OF THE INVENTION

We disclose a drug tracking system which includes a drug tag that may be identified in bodily waste. The drug tag may be a colored molecule used as a food dye which may be measured using photographic or absorption spectroscopic analysis techniques. In some embodiments, the food dye may participate in chemical and/or metabolic reactions which produce a reaction product. In these embodiments, the reaction product rather than the food dye may be measured in bodily waste.

The drug tag may be consumed separately but approximately simultaneously with the drug of interest. Alternatively, the food dye included in the drug tag may be adhered to or mixed with a drug prior to consumption. The food dye or its reaction product may be measured in bodily waste, including urine or feces, to provide a qualitative identification of the drug associated with the food dye. In some embodiments, the signal from the photographic or absorption spectroscopic analysis may be normalized to a urine metabolite or urine specific gravity to provide a quantitative assessment of drug consumption.

Each food dye may be associated with a unique drug. Therefore, the photographic analysis or emission spectra produced by analyzing a subject or patient's bodily waste may provide conclusive evidence of the identity of the consumed drug.

Some drug tags may include multiple food dyes. In some embodiments, each of the multiple food dyes may identify a member of a class. Examples of classes include drug class, manufacturer, distributer, and prescribing healthcare provider. One or more of the multiple food dyes may indicate the specific drug compound.

The drug tracking system may include a database which stores multiple signature emission spectra (spectral signatures) of the food dyes used as drug tags. Computer-readable code which may be associated with the database may compare the emission spectrum from the analysis of the subject's bodily waste with the signature emission spectra of the various food dyes. When a match is made, the drug tag including one or more food dye, and consequently, its associated drug may be identified. Statistical analysis may provide a calculated confidence of the match.

In embodiments in which the bodily waste is urine, the data from the absorption spectroscopic analysis may be normalized to either a urine analyte or urine specific gravity. This may provide more quantitative data in addition to merely qualitatively identifying the drug the subject or patient has consumed.

DETAILED DESCRIPTION OF THE INVENTION

Definitions

Figure 1:
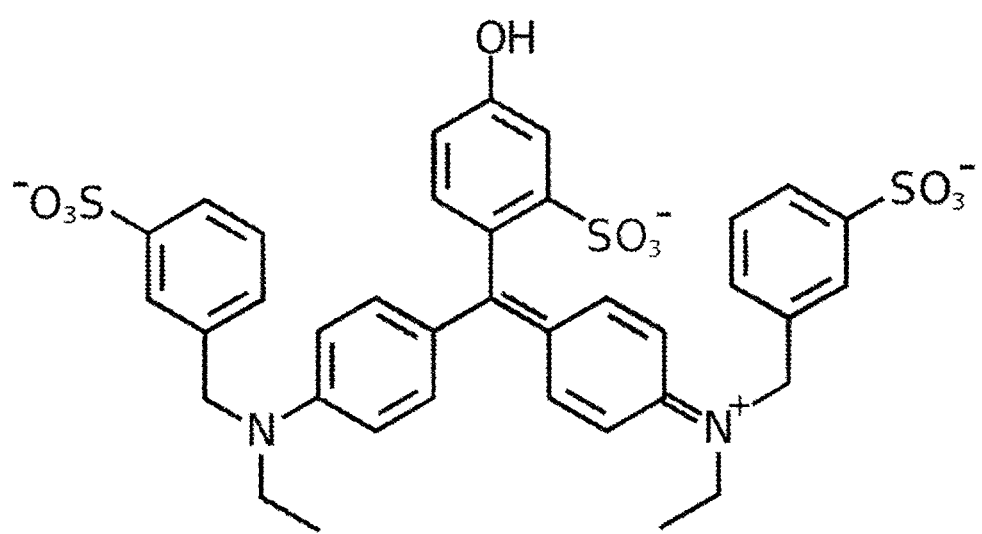
FIG. 1 shows the chemical structure of the food dye, green number 3.

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

"Drug," as used herein, means any pharmacologically active agent or mixture of agents.

"Drug consumption," as used herein, means taking a drug into the body through any method of administration, including, but not limited to, oral administration.

"Food dye," as used herein, means a molecule or compound which, when added to food, changes the color of the food. Food dyes may be those which are approved for use in food, drugs, cosmetics, or medical devices by governing regulatory bodies. "Food dye," as used herein, may also include those excluded for use in food, drugs, cosmetics, or medical devices by governing regulatory bodies. "Food dye," as used herein, may be a naturally occurring or synthetic molecule or compound.

"Spectral analysis," as used herein, means detection of light emitted from an object or substance including that which may be obtained using absorption spectroscopy or digital photography techniques. "Spectral analysis," as used herein, may be qualitative or quantitative.

"Spectral signature," as used herein means a detected signal obtained from a spectral analysis of an object or substance.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

Finally, as used herein any reference to "one embodiment" or "an embodiment" means that a particular element; feature, structure, or characteristic described in connection with the embodiment is included in at least one embodiment. The appearances of the phrase "in one embodiment" in various places in the specification are not necessarily all referring to the same embodiment.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose a drug tracking system which includes a method of tracking drug consumption by a subject or patient. One advantage of the disclosed drug tracking system is that the disclosed system does not require a technique to measure the drug or its metabolite directly. Rather the system includes colored molecules which may commonly be used as food dyes and which are used as a tag for the drug. A different food dye may be used to tag each drug. The food dye may be taken separately but in conjunction with the drug or may be applied to the drug by spraying or painting the food dye on the drug (for example, a pill), mixing the food dye with the drug, or other methods known in the art. Each tagged drug may be associated with a different food dye. Each food dye may have a different spectral signature. While the drug may separate from the food dye after consumption, the excreted food dye in bodily waste is still indicative of consumption of the particular defined drug.

Another advantage of the disclosed drug tracking system is that the food dye may be detected in bodily waste, including urine and feces, using well-established absorption spectroscopic or photographic techniques. In some embodiments, the absorption spectroscopic or photographic analysis may be conducted by analytical equipment that is housed within a medical toilet. In this embodiment, the food dye may be detected in a convenient and unobtrusive matter. The subject or patient simply urinates or defecates normally into the bowl of the medical toilet and the digital camera or spectrometer within the medical toilet qualitatively or quantitatively detects or measures the food dye.

In some embodiments, the absorption spectroscopic analysis includes exposing the urine sample to an energy source that emits a range of excitation wavelengths. The range of excitation wavelengths may span one or more of the infrared, ultraviolet, or visible light ranges. For example, those dyes which are detectable within the visible range, the excitation wavelengths may be between 390 nm and approximately 700 nm.

In some embodiments, a camera may collect digital data as the urine or feces enters the toilet. A processor within or connected to the camera may comprise instructions for analyzing the digital data to identify the one or more food dyes in the urine or feces.

Some examples of food dyes which may be used as drug trackers in the disclosed system include, but are not limited to, green number 3, red number 3, methylene blue, indigo carmine, cochineal carmine red, and tartrazine. While some food dyes do not participate in metabolism or other chemical reactions under conditions to which the drug and food dye are likely to be exposed, other food dyes form one or more reaction products. For example, red number 3, methylene blue, and cochineal carmine red may be converted to reaction products which may be measured in bodily waste to indicate drug consumption. The reaction product may require different conditions for detection using absorption spectroscopic analysis than the original food dye. For example, methylene blue is a blue colored dye that may be detected using an excitation wavelength of about 668 nm. However, its reaction product is leucomethylene which is colorless and detectable using an excitation wavelength of about 246 nm. Consequently, the absorption spectroscopic analysis used to detect a drug tagged with methylene blue may include excitation wavelengths that include both 668 nm and 246 nm.

Some food dyes change their spectroscopic properties with changes in the pH. For example, indigo carmine changes colors with change in pH. Accordingly, it may be useful to adjust the pH of the sample of urine or other bodily waste prior to analysis.

Some food dyes are not significantly absorbed in the gut and, when consumed orally, are excreted in feces. Consequently, drug tags that include these food dyes may be detected in fecal samples. Examples of food dyes that may be detected in feces include FD&C Red No. 3, FD&C Red #40, FD&C Red #40 Alum Lake, FD&C Blue #1 Alum Lake, FD&C Yellow #5 Alum Lake, FD&C Yellow #6 Alum Lake, betacyanin, and carmine.

In some embodiments, the drug tracking system includes multiple food dyes. The combination of two or more spectrally distinguishable food dyes provides greater power in identifying the drug with which it is associated. The combination of two or more food dyes in a single drug tag also results in a greater number of drug tags which may be created with a given number of food dyes. Like tags that include single food dyes, the multiple food dyes may be taken separately but in conjunction with the drug or may be applied to the drug by spraying or painting the food dyes on the drug (for example, a pill), mixing the food dye with the drug, or other methods known in the art. Alternatively, a combination of mixing the food dyes with the drug and applying the food dyes to the surface of a pill may be used to tag the drug. Furthermore, a tag may be administered with the drug by providing a food dye separately but in combination with the drug and providing another food dye applied to the drug or mixing with the drug.

In some embodiments, each of the food dyes may identify a member of a different class. For example, one of the multiple food dyes in a tag may identify the class of drugs of which the associated drug is a member. In an example, the presence of FD&C Red #40 Alum Lake may indicate that the drug is an opioid while the presence of FD&C Blue #1 Alum Lake may indicate that the drug is a selective serotonin reuptake inhibitor (SSRI). In another example, one of the multiple food dyes may identify the specific drug compound. For example, the presence of FD&C Yellow #6 Alum Lake may indicate that the drug is oxycodone while the presence of FD&C Red No. 3 may indicate that the drug is sertraline. In some examples oxycodone (an opioid) may be combined with FD&C Red #40 Alum Lake and FD&C Yellow #6 Alum Lake which may indicate both the opioid class and the member within the class, oxycodone. Likewise, sertraline (an SSRI) may be combined with FD&C Blue #1 Alum Lake and FD&C Red No. 3 which indicates that the drug is a member of the SSRI class and the member within the SSRI class, sertraline. Additional food dyes may be associated with additional classes which may include manufacturer, distributer, prescribing healthcare provider, or production lot.

As a result of the photographic or absorption spectroscopic analysis of the bodily waste, the system produces spectral signature. The spectral signature may be entered into a database which stores the signature spectral signatures from multiple food dyes which may be used as drug tags. A computer-readable medium which may associated with the database may compare the spectral signature produced from the photographic or absorption spectroscopic analysis of the bodily waste with the spectral signatures of the food dyes stored in the database. When a match between the spectral signature from the analysis of the bodily waste and a spectral signature in the database is made, the drug associated with the food dye that produces the spectral signature may be identified. In some embodiments, the drug identified using the drug tracking system may be compared to a list of medications which have been prescribed to the subject or patient. The user may therefore confirm whether the subject or patient has consumed the proper medications. This may be useful for patient care and in clinical trials where a clinical researcher needs to know whether the subject was compliant with taking the study medication. The disclosed system may also be useful to keep clinical researchers blind as to which subjects received the drug and which received placebo. The food dye may be measured by a technician who is not part of the clinical trial so as not to bias the study.

In some embodiments, a first absorption spectroscopic analysis, which may be conducted using a range of excitation wavelengths, may produce an emission spectrum with one or more peaks at certain emission wavelengths. One or more follow-up absorption spectroscopic analysis may then be conducted on the same sample. The follow-up absorption spectroscopic analysis may include a single excitation wavelength that may be calculated to be the maximum excitation wavelength which resulted in the peak shown on the emission spectrum. A follow-up absorption spectroscopic analysis may be performed for each peak in the emission spectrum. The one or more follow-up absorption spectroscopic analyses may provide clearer spectroscopy data without overlapping peaks, particularly when the subject has consumed more than one drug that has been tagged with a different food dye. The emission spectra may then be entered into the database, compared to signature emission spectra of a variety of food dyes that are used as drug tags. The one or more drugs the subject has consumed may then be identified by determining the one or more drugs associated with the matching emission spectra.

Urine from a subject or patient may be more or less dilute depending on the hydration status of the subject or patient. Consequently, it may be useful to normalize the signal obtained from measuring a food dye or its reaction product (which may be area under the curve or height of the emission peak) to produce more quantitative data. For example, a urine metabolite may be used to normalize the signal from the emission spectra. Alternatively, urine specific gravity may be used to normalize the spectroscopy data.

The drug tagging system may include a database. The database may include a memory which may store the spectral signature associated with each of the plurality of drug tags and/or each of the food dyes included in the drug tags. In addition, or in the alternative, the memory may store the identity of each of the one or more food dyes included in each of the plurality of drug tags. Furthermore, the database may store the identity of the drug and/or the member of a class to which the drug belongs. The association of each drug or class with each spectral signature, food dye, or combination of food dyes may also be stored in the memory.

The database may be in electronic connection with non-transitory computer-readable medium. The non-transitory computer-readable medium may be stored on the same processor as the database or on a separate remote processor that is in electronic communication with the processor that stores the database. The non-transitory computer-readable medium may include instructions for conducting a comparison of a photographic or absorption spectroscopic analysis of bodily waste with the spectral signature associated with each of the plurality of food dyes or the plurality of drug tags. The instructions may also direct a statistical analysis of the comparison to provide an assessment of the confidence of the match. In an example, when a sample of bodily waste is analyzed by photographic or spectroscopic techniques, the data may be transmitted to the database and compared with stored data of the spectral signature of each of the drug tags. The identity of the drug tag present in the bodily waste may then be identified. The drug consumed by the individual who provided the bodily waste may be determined by cross-referencing the drug tag with its associated drug.

Figure 2:
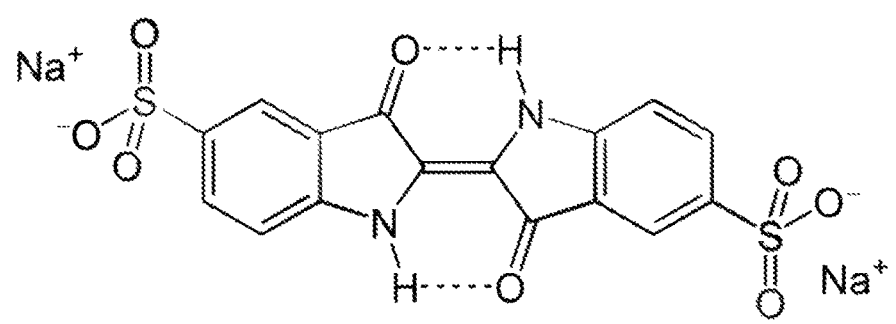
FIG. 2 shows the chemical structure of the food dye, indigo carmine.
Figure 3:
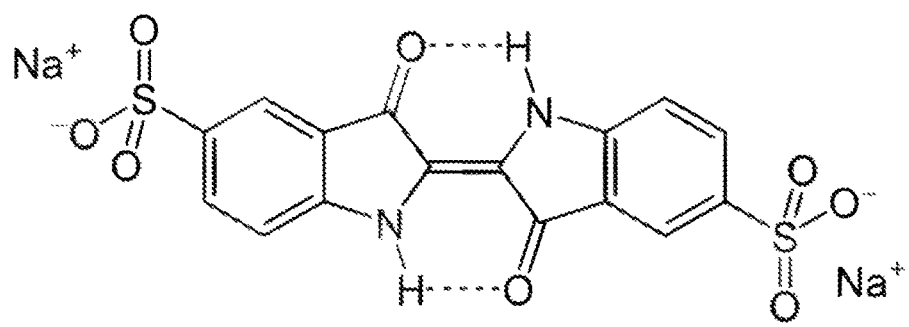
FIG. 3 shows the chemical structure of the food dye, tartrazine.
Figure 4:
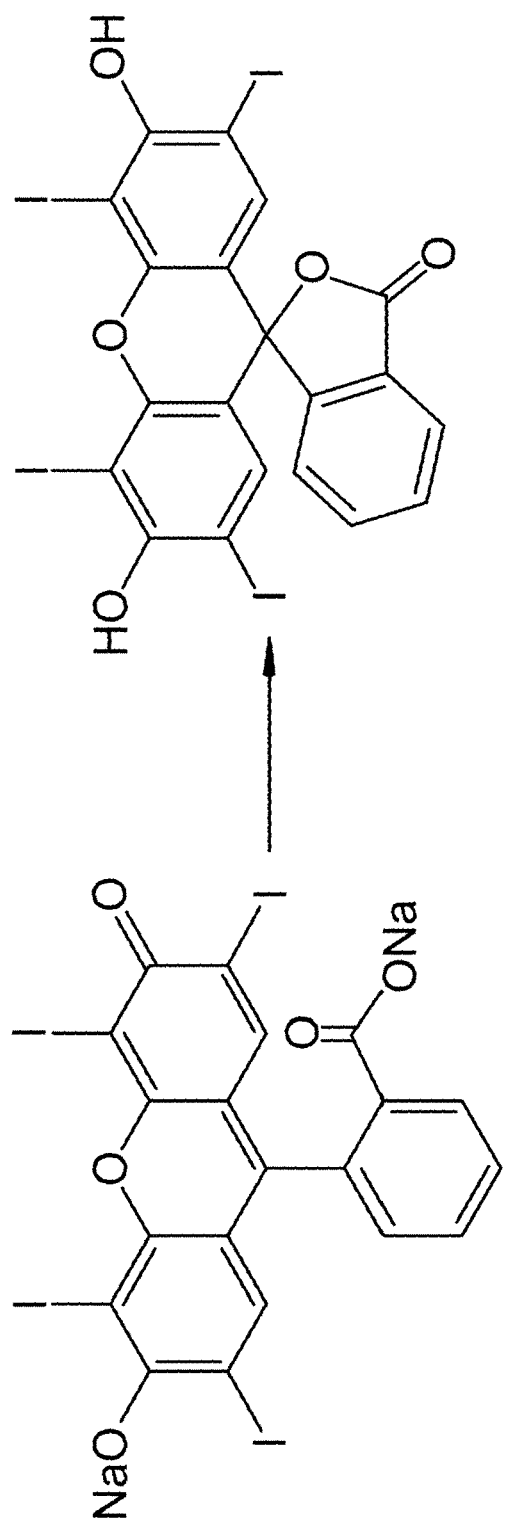
FIG. 4 shows the chemical structure of the food dye, red number 3 and its reaction product.
Figure 5:
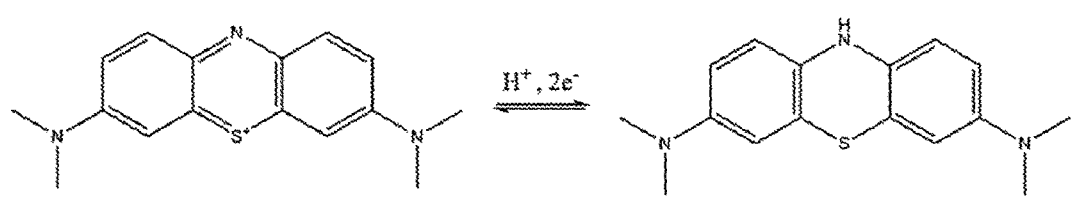
FIG. 5 shows the chemical structure of the food dye, methylene blue and its reaction product, leucomethylene blue.
Figure 6:
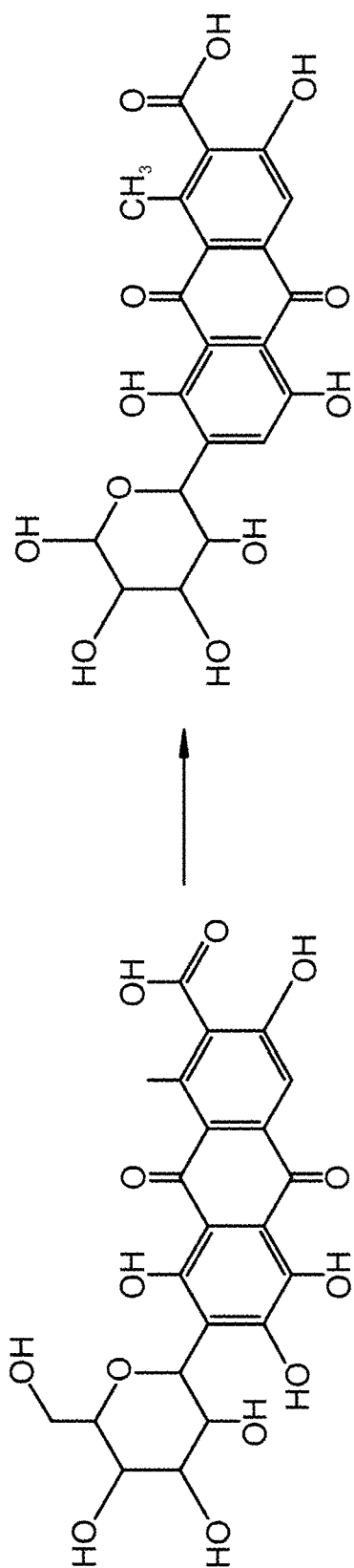
FIG. 6 shows the chemical structure of the food dye cochineal carmine red and its reaction product.

Referring now to the drawings, FIG. 1-6 include the chemical structures of food dyes which may be used as drug tags according to the disclosure. FIGS. 4-6 also show reaction products of the food dyes which may be detected in urine to indicate consumption of the drug that was tagged with the food dye.

FIG. 1 shows the chemical structure of the common food dye, green number 3. Green number 3 is not known to be metabolized. Therefore, green number 3 may be used as a drug tracking molecule and measured in urine directly. Green number 3 has a peak absorption wavelength of about 625 nm which is within the visible range.

FIG. 2 shows the chemical structure of the common food dye, indigo carmine. Indigo Carmine is excreted mostly intact. However, the color, and therefore, the absorption spectra, of indigo carmine is pH dependent. Therefore, it may be useful to adjust the pH of the urine sample prior to measuring indigo carmine according to an embodiment of the disclosure. Indigo carmine has a peak absorption wavelength of about 609 nm, within the visible range.

FIG. 3 shows the chemical structure of the common food dye, tartrazine, also known as FD&C Yellow 5 and E102. Tartrazine has a peak absorption wavelength in aqueous solution of about 425 nm, within the visible range. Metabolism of tartrazine depends on the route of administration. Tartrazine is excreted unchanged when administered intraperitoneally. Oral administration results in about half of the tartrazine dose is converted to sulphanilic acid by intestinal microflora although very little sulphanilic acid is excreted in urine after tartrazine consumption.

FIG. 4 shows the chemical structure of the common food dye, red number 3, also known as erythrosine, and its reaction product. Red dye number 3 has a peak absorption wavelength of about 530 nm, within the visible range.

FIG. 5 shows the chemical structure of methylene blue and its reaction product, leucomethylene blue. Methylene blue is a blue colored dye with a peak absorption wavelength of about 664 nm. It becomes reversibly reduced to leucomethylene blue which is colorless. Leucomethylene blue has a peak absorption wavelength of about 246 nm, which is outside the visible range but readily detectable with spectrophotometric methods using excitation wavelengths in the ultraviolet range.

FIG. 6 shows the chemical structure of cochineal carmine red and its metabolite. Cochineal carmine red has a peak absorption wavelength of about 513 nm, within the visible range. Conchineal carmine red is excreted both in the urine and feces.

Figure 7:
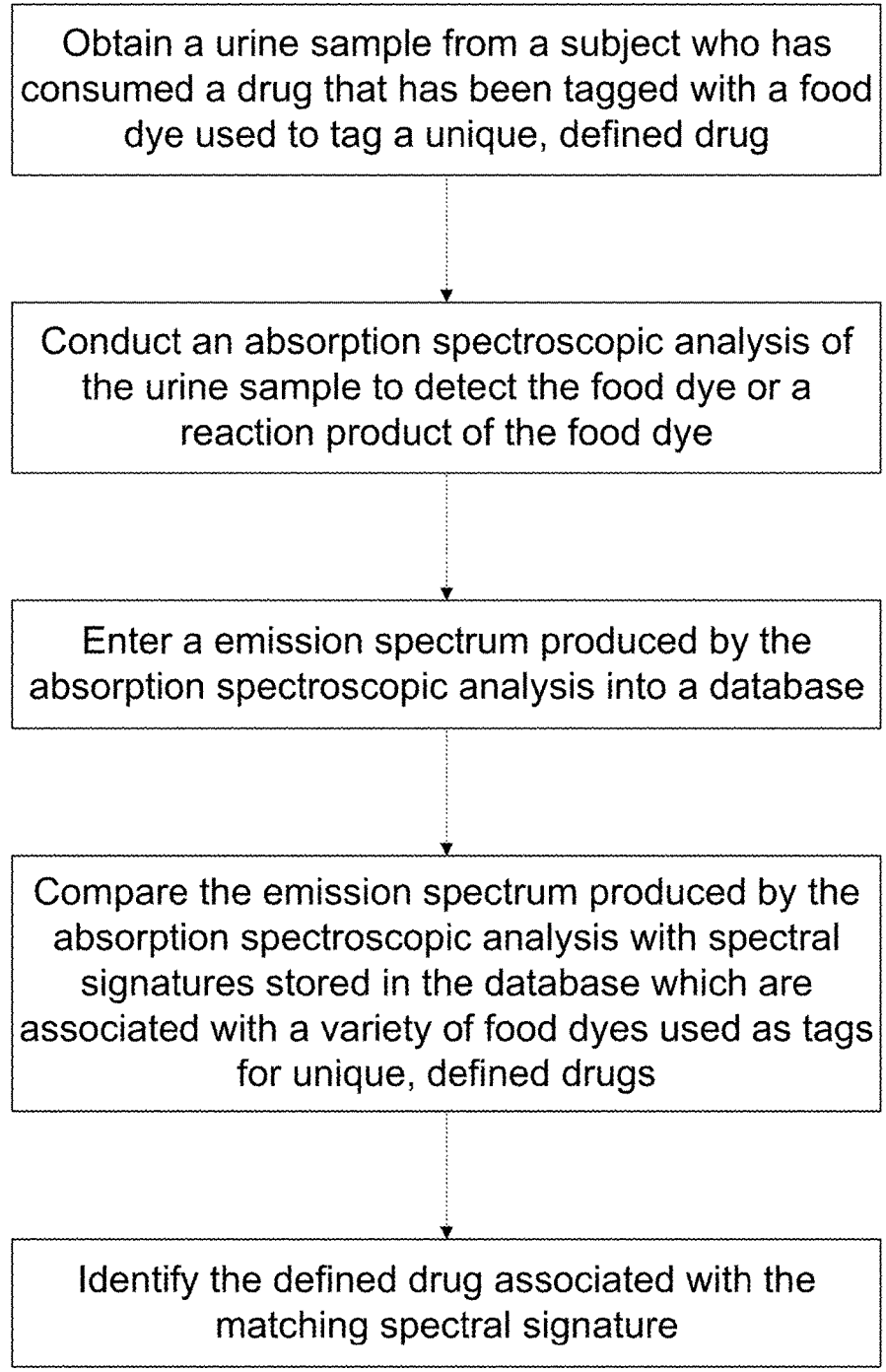
FIG. 7 provides a flow chart which includes steps in an embodiment of a method of using the disclosed drug tracking system.

FIG. 7 presents a flow chart describing a method of using food dyes in a drug tagging system as disclosed herein. A subject first consumes a drug that has been tagged with a food dye. The food dye is used as a tag only for the drug the subject has consumed. The food dye or its reaction product may be detected in the subject's urine using an absorption spectroscopic technique. A user then obtains a sample of the subject's urine and analyzes the urine using an absorption spectroscopic technique. The absorption spectroscopic technique uses a range of multiple excitation wavelengths and produces an emission spectrum which has a peak representing a maximum emission wavelength. The user enters the emission spectrum into a database in which the emission spectra of multiple food dyes that are used as drug tags are stored. These emission spectra represent the signature emission spectra of the food dyes. The database also includes the identity of the drug which is tagged with the food dye associated with the signature emission spectra. Using computer readable medium associated with the database, the user compares the emission spectrum with the signature emission spectra in the database and finds a match. The user then determines which drug is associated with the food dye that has the matching signature emission spectra. This information is also stored in the database.

Figure 8:
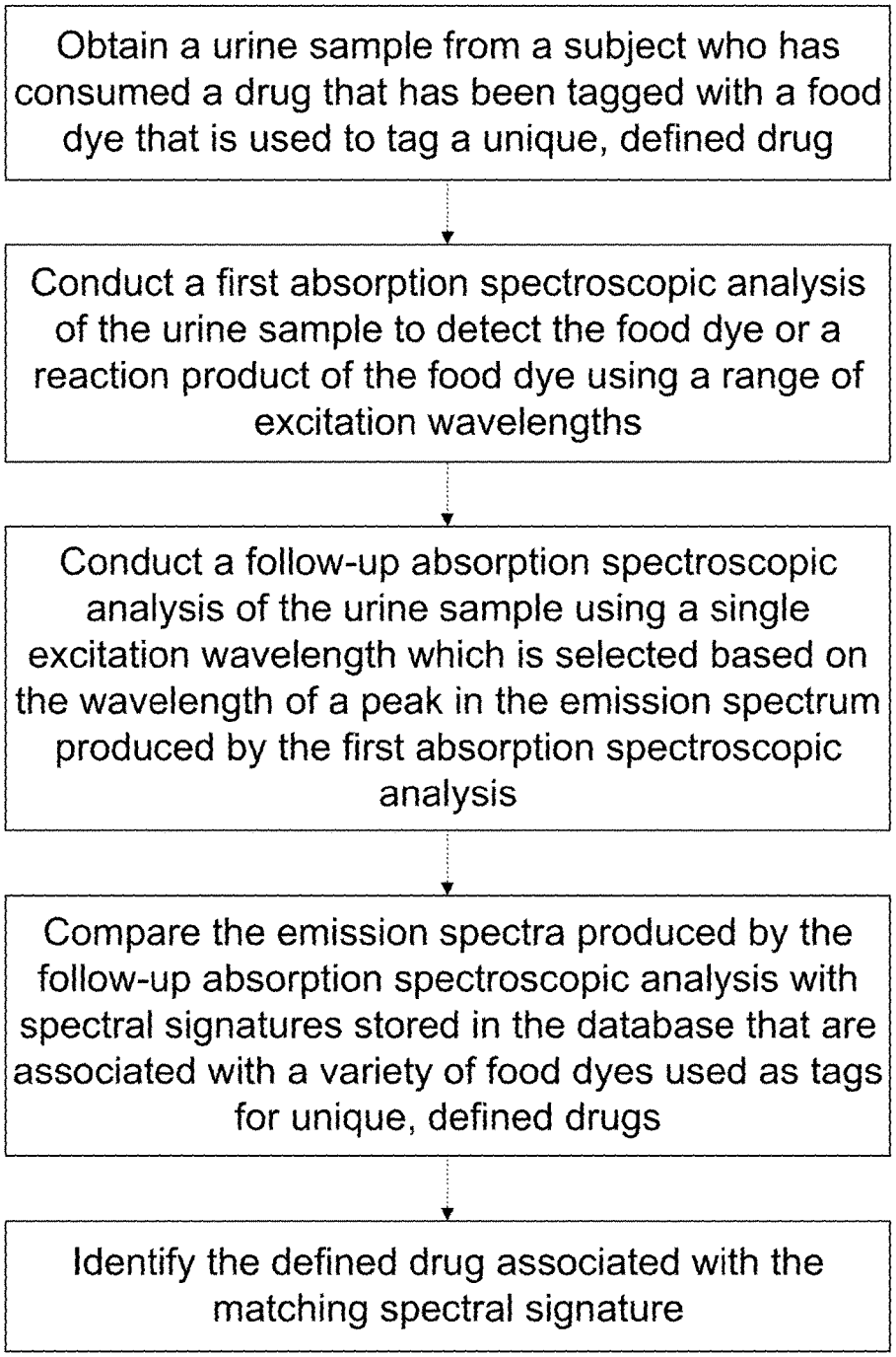
FIG. 8 provides a flow chart which includes steps in an embodiment of a method of using the disclosed drug tracking system.

FIG. 8 presents a flow chart in which a follow-up spectral analysis is used to confirm the identity of the food dye and, consequently, the associated drug. The method begins as the method described in FIG. 7 with a subject consuming a drug that has been tagged with a food dye according to the disclosure. A user then obtains a sample of the subject's urine and analyzes the urine using an absorption spectroscopic technique. The absorption spectroscopic technique uses a range of multiple excitation wavelengths and produces an emission spectrum which has a peak representing a maximum emission wavelength. The urine is then analyzed by conducting a follow-up absorption spectroscopic analysis. The follow-up absorption spectroscopic analysis uses a single excitation wavelength. The single excitation wavelength is calculated based on the wavelength of the peak in the emission spectrum. The emission spectrum that results from the follow-up absorption spectroscopic analysis may include less background from other components in the urine thereby confirming the wavelength of the peak associated with the food dye. A separate follow-up absorption spectroscopic analysis may be conducted using single wavelengths extrapolated from an additional peak in the first emission spectrum. Consequently, the identity of an emission peak resulting from a second food dye associated with a second drug may be confirmed. The one or more follow up spectra may then be entered into the database, compared to signature emission spectra of food dyes used as drug tags, and the identity of their associated drugs revealed.

Table 1 is a non-inclusive list of food dyes which may be included in drug tags according to the disclosed drug tracking system. These include both natural and synthetic food dyes. The list includes food dyes whose nomenclature is as adopted by the United States Food and Drug Administration (FDA). Those names that include the acronym "FD&C" are listed by FDA for use in food, drugs, and cosmetics. Those names that include the acronym "D&C" are listed by FDA for use in drugs and cosmetics. Those names that include the term "Ext. D&C" are no longer authorized for use by FDA.

Color additives are classified as either straight colors, lakes, or mixtures thereof. Straight colors or those that have neither been mixed nor chemically reacted with other substances. Lakes are those that are synthesized by chemically reacting a straight color with precipitants and substrata. While other metallic salts may be used, typically, lakes that are used for coloring food products are synthesized by using aluminum cation as the precipitant and aluminum hydroxide as the substratum. Barrows, Julie, N., Lipman, Arthur L., and Bailey, Catherine J. (2003) Color Additives: FDA's Regulatory Process and Historical Perspectives. *Food Safety Magazine*, October/November.

TABLE 1

1,4-Bis[(2-hydroxyethyl)amino]-9,10-anthracenedione
bis(2-propenoic) ester copolymers
1,4-Bis[(2-methylphenyl)amino]-9,10-anthracenedione
1,4-Bis[4-(2-methacryloxyethyl)phenylamino]-9,10-
anthraquinone copolymers
16,17-Dimethoxydinaptho[1,2,3-cd:3',2',1'-lm]
perylene-5,10-dione
16,23-Dihydrodinaptho[2,3-a:2',3'-i]napth[2',3':6,7]
indolo[2,3-c]carbazole-5,10,15,17,22,24-hexone
2-[[2,5-Diethoxy-4-[(4-methylphenyl)thio]phenyl]azo]-
1,3,5-benzenetriol
4-[(2,4-Dimethylphenyl)azo]-2,4-dihydro-5-methyl-2-
phenyl-3H-pyrazol-3-one
4-Methyl-7-diethylaminocoumarin (MDAC)
7,16-Dichloro-6,15-dihydro-5,9,14,18-anthrazinetetrone
Algae meal, dried
Alkanet (Alkane)
Alloxan
Alumina
Aluminum powder
Annatto extract TABLE 1-continued Astaxanthin
Astaxanthin dimethyldisuccinate
Betacyanin
Beet juice (as vegetable juice)
Beet powder (as dehydrated beets)
Beta carotene, natural and synthetic
Beta-Apo-8'carotenal
Beta-carotene
Bismuth citrate
Bismuth oxychloride
B-Methyl umbelliferone
Bone Black
Bronze powder
C.I. Vat Orange 1
Calcium carbonate
Canthaxanthin
Caramel
Carbazole violet
Carbon black
Carbon black (channel process)
Charcoal-NF XI
Carmine
Carminic acid
Carrot oil
Charcoal
Chlorophyll copper complex
Chlorophyllin-copper complex
Chromium hydroxide, green
Chromium oxides greens
Chromium-cobalt-aluminum oxide
Citrus Red #2
Cobaltous aluminate (Cobalt Blue)
Cochineal
Cochineal extract
Copper, metallic powder
Corn endosperm oil
Cottonseed flour, toasted partially defatted cooked
Cudbear
D&C Black #1
D&C Black #2
D&C Black #3
D&C Blue #4
D&C Blue #6
D&C Blue #7
D&C Brown #1
D&C Green #5
D&C Green #6
D&C Green #7
D&C Green #8
D&C Lakes
D&C Orange #10
D&C Orange #11
D&C Orange #14
D&C Orange #15
D&C Orange #16
D&C Orange #17
D&C Orange #3
D&C Orange #4
D&C Orange #5
D&C Orange #8
D&C Red #10
D&C Red #11
D&C Red #12
D&C Red #13
D&C Red #14
D&C Red #17
D&C Red #18
D&C Red #19
D&C Red #21
D&C Red #22
D&C Red #24
D&C Red #27
D&C Red #28
D&C Red #29
D&C Red #30
D&C Red #31
D&C Red #33
D&C Red #34
D&C Red #35
D&C Red #36

TABLE 1-continued

D&C Red #37
D&C Red #38
D&C Red #39
D&C Red #5
D&C Red #6
D&C Red #7
D&C Red #8
D&C Red #9
D&C Violet #2
D&C Yellow #10
D&C Yellow #11
D&C Yellow #7
D&C Yellow #8
Dihydroxyacetone
Disodium EDTA-copper
Ext. D&C Blue #1
Ext. D&C Blue #4
Ext. D&C Green #1
Ext. D&C Lakes
Ext. D&C Orange #1
Ext. D&C Orange #3
Ext. D&C Orange #4
Ext. D&C Red #1
Ext. D&C Red #2
Ext. D&C Red #3
Ext. D&C Red #8
Ext. D&C Red #10
Ext. D&C Red #11
Ext. D&C Red #13
Ext. D&C Red #14
Ext. D&C Red #15
Ext. D&C Violet #2
Ext. D&C Yellow #1
Ext. D&C Yellow #10
Ext. D&C Yellow #3
Ext. D&C Yellow #5
Ext. D&C Yellow #6
Ext. D&C Yellow #7
Ext. D&C Yellow #9
FD&C Blue #1 and its Aluminum Lake
FD&C Blue #2
FD&C Blue #2 Aluminum Lake on alumina
FD&C Green #1
FD&C Green #2
FD&C Green #3
FD&C Lakes
FD&C Red #1
FD&C Red #2
FD&C Red #3
FD&C Red #4
FD&C Red #40 and its Aluminum Lake
FD&C Violet #1
FD&C Yellow #5 and its Aluminum Lake
FD&C Yellow #6 and its Aluminum Lake
Ferric ammonium ferrocyanide (Iron Blue)
Ferric chloride
Ferric ferrocyanide (Iron Blue)
Ferros lactate
Ferrous gluconate
Ferrous sulfate
Fruit juice
Fuller's earth
Fustic
Gloss white
Gluaiazulene (Azulene)
Grape color extract
Grape skin extract (enocianina)
Graphite
Guanine (Pearl essence)
Haematococcus algae meal
Henna
Iron oxides
Kieselguhr (Diatomite)
Lead acetate
Lithopone
Logwood (Gluewood, Campeche wood)
Logwood, chips & extract
Luminescent zinc sulfide
Lycopene, tomato extract or concentrate
Manganese Violet TABLE 1-continued Mica
Mica-based pearlescent pigment
N,N'-(9,10-Dihydro-9,10-dioxo-1,5-anthracenediyl) bis-benzamide
Paprika & Paprika oleoresin
*Paracoccus* pigment
Phaffia yeast
Potassium ferrocyanide
Potassium sodium copper chlorophyllin (Chlorophyllin copper complex)
Pyrophyllite
Riboflavin
Safflower (American saffron)
Saffron
Sienna
Silver
Sodium copper chlorophyllin
Spirulina extract
Synthetic iron oxide
Tagetes (Aztec marigold) meal and extract
Talc
Titanium dioxide
Tumeric & Tumeric oleoresin
Ultramarine blue
Ultramarines (Blue, Green, Pink, Red, & Violet)
Umber
Vegetable juice
Vermiculite
Yellow #5 and its Aluminum Lake
Yellow #6
Zinc oxide
Zirconium oxide
Zirconium silicate While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A drug tracking system comprising:
a plurality of drugs;
a plurality of drug tags, wherein each of the plurality of drug tags comprises a plurality of food dyes; wherein each of the plurality of drugs is associated with one of the plurality of drug tags when the plurality of drugs and the plurality of drug tags are combined with one another;
wherein each of the plurality of drug tags produces a spectral signature detectable by either photographic or absorption spectroscopic analysis;
wherein the spectral signature produced by each of the plurality of drug tags is distinguishable from others within the plurality of drug tags;
wherein at least one of the plurality of food dyes within each of the plurality of drug tags identifies a member of a class within which at least one of the plurality of drugs belongs;
wherein at least one other of the plurality of food dyes within each of the plurality of drug tags identifies specifically what at least one of the plurality of drugs is; and
wherein the spectral signature is detectable in bodily waste.

2. The drug tracking system of claim 1, wherein at least one of the plurality of food dyes in each of the plurality of drug tags is mixed with or adhered to a surface of at least one of the plurality of drugs.

3. The drug tracking system of claim 1, further comprising a database comprising the spectral signature associated with each of the plurality of drug tags and each of the plurality of drugs associated with each of the plurality of drug tags.

4. The drug tracking system of claim 3, wherein the database further comprises a list of each of the plurality of food dyes comprising each of the plurality of drug tags.

5. The drug tracking system of claim 3, wherein the database is accessible by a remote processor.

6. The drug tracking system of claim 3, wherein the database further comprises non-transitory computer-readable medium comprising instructions for conducting a comparison of a spectral analysis of bodily waste with the spectral signature associated with each of the plurality of drug tags.

7. The drug tracking system of claim 6, wherein the non-transitory computer-readable medium comprises instructions for conducting a statistical analysis of the comparison.

8. The drug tracking system of claim 1, wherein a metabolite of at least one of the plurality of food dyes is detectable in feces.

9. The drug tracking system of claim 1, wherein each of the plurality of food dyes is detectable in feces.

10. The drug tracking system of claim 9, wherein the plurality of food dyes comprises two or more of FD&C Red No. 3, FD&C Red #40, FD&C Red #40 Alum Lake, FD&C Blue #1 Alum Lake, FD&C Yellow #5 Alum Lake, FD&C Yellow #6 Alum Lake, betacyanin, and carmine.

11. The drug tracking system of claim 10, wherein the spectral signature produced by each of the plurality of drug tags is produced by a range of excitation wavelengths comprising a plurality of wavelengths between approximately 390 nm and approximately 700 nm.

12. The drug tracking system of claim 9, wherein the plurality of food dyes comprises two or more of FD&C Red No. 3, FD&C Red #40, FD&C Red #40 Alum Lake, FD&C Blue #1 Alum Lake, FD&C Yellow #5 Alum Lake and FD&C Yellow #6 Alum Lake.

13. The drug tracking system of claim 1, wherein the plurality of food dyes is detectable in urine.

14. The drug tracking system of claim 13, wherein the spectral signature produced by each of the plurality of drug tags is produced by a range of excitation wavelengths comprising a plurality of wavelengths between approximately 390 nm and approximately 700 nm.

15. The drug tracking system of claim 1, wherein at least one of the plurality of food dyes comprises a color additive absorbed onto a metallic salt.

16. The drug tracking system of claim 15, wherein the metallic salt comprises alumina.

17. The drug tracking system of claim 1, wherein each of the plurality of food dyes is synthetic.

18. The drug tracking system of claim 1, wherein the plurality of food dyes comprises at least three food dyes.

* * * * *